United States Patent [19]

Mechin

[11] Patent Number: 4,552,802

[45] Date of Patent: Nov. 12, 1985

[54] SELF-ADHESIVE PRODUCT, PROCESS FOR ITS MANUFACTURE AND APPLICATION AS A DRESSING, PACKING SHEET OR FIXING TAPE

[76] Inventor: Jean-Claude Mechin, 109 Boulevard Malesherbes, 75008 Paris, France

[21] Appl. No.: 514,220

[22] Filed: Jul. 15, 1983

[51] Int. Cl.[4] .......................... B32B 7/12; B05D 5/10; C09J 7/02
[52] U.S. Cl. .................................. 428/255; 128/156; 128/169; 427/207.1; 427/314; 427/374.1; 428/290; 428/317.3; 428/317.7; 428/343; 428/355; 428/356
[58] Field of Search ................. 524/519, 62; 428/246, 428/40, 343, 355, 290, 356, 255, 317.3, 317.7; 128/156, 169; 427/207.1, 314, 374.1

[56] References Cited

U.S. PATENT DOCUMENTS

| | | | |
|---|---|---|---|
| 2,884,400 | 4/1959 | Moore | 524/519 |
| 3,162,610 | 12/1964 | Samour | 428/356 |
| 3,741,856 | 6/1973 | Hurst | 428/246 |
| 3,919,148 | 11/1975 | Winters et al. | 524/62 |
| 4,112,177 | 9/1978 | Salditt et al. | 428/355 |
| 4,307,717 | 12/1981 | Hymes et al. | 128/156 |
| 4,427,737 | 1/1984 | Cilento et al. | 428/343 |

*Primary Examiner*—Thomas J. Herbert
*Attorney, Agent, or Firm*—Sughrue, Mion, Zinn, Macpeak, and Seas

[57] ABSTRACT

The invention relates to a new self-adhesive product in the form of a sheet, band or tape.

It comprises a cellular support coated with a layer of synthetic or natural elastomer previously treated by heating to a temperature between 70° and 160° C., followed by cooling.

Application as dressing, packing sheet or fixing tape.

14 Claims, No Drawings

SELF-ADHESIVE PRODUCT, PROCESS FOR ITS MANUFACTURE AND APPLICATION AS A DRESSING, PACKING SHEET OR FIXING TAPE

BACKGROUND OF THE INVENTION

The present invention relates to a new fastening device, and more particularly a new self-adhesive product in the form of a sheet, band or tape, a process for its manufacture, and its application as a dressing, packing sheet and fixing tape.

In the field of dressings and of packing, in particular, various self-adhesive products are known which are generally in the form of tapes. These tapes adhere to the majority of surfaces with which they can be brought in contact, which is often a disadvantage. On the other hand, the non-adhesive products employed, for example, for typing parcels or packets must be fixed by stapling or knotting, which complicates their use and involves loss of time. Self-adhesive tapes whose surfaces can be made adhesive by moistening are also known, but the adhesive strength is generally insufficiently high.

SUMMARY OF THE INVENTION

The present invention relates to a self-adhesive product in the form of a sheet, band or tape which can be positioned quickly and easily, without the need to use any accessory.

The invention further relates to the application of a new self-adhesive product as a packing sheet, fixing tape or dressing.

The invention also relates to a process permitting the manufacture of a new self-adhesive product by coating a synthetic or natural elastomer on a cellular support.

DETAILED DESCRIPTION OF THE INVENTION

The self-adhesive product according to the invention of the type comprising a support coated with at least one self-adhesive layer consists of a cellular support coated with a layer of synthetic or natural elastomer, previously treated by heating at a temperature between 70° and 160° C., followed by cooling, according to the process described below.

The support can consist of any sheet or tape of a cellular material, for example of a band or gauze, or a flexible sheet made of a synthetic or natural material comprising perforations. The dimension of the cells of the support is smaller than approximately 1 cm, and preferably between 1 and 3 mm, but it can be smaller still.

The elastomer coated on the support is a synthetic or natural elastomer, for example a natural rubber available in the trade in the form of a pale crêpe, brown crêpe or smoked sheet, according to the type. According to the invention, it is preferred to employ a natural rubber of the pale crêpe type.

It is also possible to employ a synthetic elastomer and particularly cis-1,4-polyisoprene, a butadiene-styrene copolymer, a cis-1,4-polybutadiene, a polyoxypropylene, a polyoxychloropropylene, a polyacrylate, or the like, or a derivative or a graft polymer or graft copolymer. According to the invention it is preferred to employ a butadiene-styrene copolymer obtained by polymerization of butadiene and styrene in the presence of a persulfate catalyst, cis-1,4-polyisoprene obtained by stereospecific polymerization in the presence of a catalyst based on titanium tetrachloride and triethylaluminum or triethyllithium (a catalyst of the Ziegler-Natta type), or cis-1,4-polybutadiene obtained by stereospecific polymerization in the presence of triethylaluminum and a cobalt salt or titanium tetraiodide.

If need be, the elastomer can be colored in bulk by the addition of a colorant. A figurative pattern or an inscription can also be applied to each of the faces by printing.

According to the process of the invention, the elastomer is heated for approximately 30 min to 2 hours, at a temperature between 70° and 160° C., and preferably between 80° and 100° C., is allowed to cool to a temperature below approximately 50° C., is next immersed in an appropriate solvent which is allowed to stand for at least 6 hours, and is kneaded to obtain a doughy product which is coated on the support.

The temperature at which the elastomer is heated is preferably of the order of 80° to 100° C. as indicated above, but can vary depending on the nature and purity of the elastomer employed. If the temperature is too high the polymer chains are destroyed and the product degrades, while if the temperature is not sufficiently high the dissolution in the solvent is inadequate.

It is advantageous for the elastomer to be in the form of plates or thin sheets, which are employed in an amount of approximately 5 to 50 g and preferably 10 to 30 g per liter of solvent.

The solvent can be an organic solvent such as an aliphatic solvent, for example diethyl ether or dimethyl ether, or an aromatic solvent, for example phenol, naphthol, benzene, toluene or the like; it is possible to employ a chlorinated solvent such as carbon tetrachloride or chloroform.

The dough obtained after kneading, for approximately 5 to 20 minutes, is spread on the support by conventional techniques, and is then dried, for example by passing hot air, to evaporate the remaining solvent. The coating can, for example, be carried out manually by means of a doctor, or mechanically by causing the support, for example a tape of gauze, to pass through a tub containing the dough, and then between two pressing rollers which permit the thickness of the layer to be adjusted.

The thickness of the layer after drying can be limited if required to a low value of less than 1 mm.

When it has been coated, the sheet or the band serving as a support is covered with an interleaving sheet of paper, for example an embossed or thin paper, and is then wound onto itself to be stored. The coated self-adhesive product does not adhere to the interleaving paper, and can be kept flat or in a roll for an extended period.

The self-adhesive product according to the present invention offers the advantage of adhering to practically no product other than itself. It can therefore be employed in various applications where it is necessary to have a wrapping product capable of being held in place without sticking to the parts with which it is in contact.

The self-adhesive product according to the invention can particularly be employed in human or veterinary medicine as a dressing or as a bandage applied, for example, to a limb or a finger, or to the paw of an animal. It is very particularly advantageous in such an application because it is chemically inert and adheres neither to the skin, nor to hair, nor to the wound.

In addition, it is possible to incorporate in the elastomer layer, or to apply to its surface, various medicinal substances, such as antihemorrhagics, disinfectants, anodines or antibiotics, without altering its physical and chemical properties. Such a dressing cannot however be employed on a surface which is not closed.

The self-adhesive product according to the invention can also be employed in the field of packing, as a packing sheet intended, for example, for wrapping parcels without any accessory fixing device. The indications required to identify the parcel or figurative patterns can be applied by direct printing or in the form of labels glued to its surface.

It can also be employed in the form of a fixing tape of the type forming at least one loop, for tying up fragile objects to which it must not adhere, such as textiles or clothes; its self-adhesive character enables immediate fastening by simple contact with itself when it forms a loop, which avoids having to fix it with a knot or by glueing or stapling. In addition, its high self-adhesive strength guarantees against any risk of tearing away during handling, and it leaves no trace on the objects with which it can come into contact. It can in particular be used in unrolling-cutting devices currently employed for adhesive tapes.

By way of a non-limiting example, the preparation of a self-adhesive band which can be used as a dressing is described below.

EXAMPLE 300 g of cis-1,4-polyisoprene in the form of thin sheets a few millimeters thick are heated in an oven for 90 minutes at 90° C.

The cis-polyisoprene is taken out of the oven, is left to cool down to approximately 25° C., is added to 20 liters of diethyl ether and is left to stand for approximately 12 hours. It is then kneaded for approximately 15 minutes, until a doughy product is obtained, to which an antiseptic is added. The dough is coated on a gauze, at a rate of approximately 500 g per square meter of gauze, and is then dried under a stream of warm air at 22° C. for 2 minutes.

The dry thickness of the coated layer is approximately 0.5 mm. The whole is then cut up into bands to form dressings.

I claim:

1. A self-adhesive product in the form of a sheet, band or tape comprising a support coated with at least one self-adhesive layer, which adheres to practically no product, including skin and hair, other than itself, which includes a cellular support coated with a layer of synthetic or natural elastomer previously treated by heating at a temperature between 70° and 160° C., followed by cooling.

2. The self-adhesive product as claimed in claim 1, wherein the elastomer is a natural rubber or cis-1,4-polyisoprene, a butadiene-styrene copolymer, a cis-1,4-polybutadiene, a polyoxypropylene, a polyoxychoropropylene or a polyacrylate.

3. The self-adhesive product as claimed in either of claims 1 and 2, wherein the support consists of a band of gauze.

4. A packing sheet which consists of a self-adhesive product as claimed in any of claims 1, 2 or 3, in the form of a sheet.

5. A fixing tape of the type forming at least one loop, which consists of a self-adhesive product as claimed in any of claims 1, 2 or 3, in the form of a tape.

6. A dressing which consists of a self-adhesive product as claimed in any of claims 1, 2 or 3, in the form of a band.

7. The dressing as claimed in claim 6, wherein the layer of elastomer is impregnated with a medicinal active principle.

8. A process for the manufacture of a self-adhesive product in the form of a sheet, band or tape, comprising a cellular support coated with at least one self-adhesive layer, which adheres to practically no product, including skin and hair, other than itself, wherein a synthetic or natural elastomer is heated at a temperature between 70° and 160° C., is cooled to a temperature below 50° C., is immersed in a solvent which is left to stand and is then kneaded to obtain a doughy product which is coated on the support.

9. The process as claimed in claim 8, wherein the solvent is diethyl ether, dimethyl ether, phenol, naphthol, benzene, toluene, carbon tetrachloride or chloroform.

10. The process as claimed in claim 8, wherein 10 to 30 g of elastomer are employed per liter of solvent.

11. The process as claimed in claim 8, wherein the elastomer is a natural rubber or cis-1,4-polyisoprene, a butadiene-styrene copolymer, a cis-1,4-polybutadiene, a polyoxypropylene, a polyoxychloropropylene or a polyacrylate.

12. The process as claimed in either of claims 8 and 9, wherein the elastomer is heated at a temperature between 80° and 100° C.

13. A self-adhesive product in a form of a sheet, band or tape made by the process of claim 8.

14. A self-adhesive product in a form of a dressing or bandage for use in human or veterinary medicine which does not adhere to skin, hair or a wound, manufactured by a process comprising coating a cellular support with at least one self-adhesive layer, wherein a synthetic or natural elastomer is heated at a temperature between 70° and 160° C., is cooled to a temperature below 50° C., is immersed in a solvent which is left to stand and is then kneaded to obtain a doughy product which is coated on the support as said self-adhesive layer.

* * * * *